United States Patent [19]
Miller et al.

[11] Patent Number: 5,163,027
[45] Date of Patent: Nov. 10, 1992

[54] CALIBRATION BLOCK AND METHOD FOR AN ULTRASONIC SYSTEM

[75] Inventors: James T. Miller, Marietta; Bonner W. Staff, Kennesaw, both of Ga.; Christopher M. Fortunko, Newport Beach, Calif.

[73] Assignee: Lockheed Corporation, Calabasas, Calif.

[21] Appl. No.: 854,937

[22] Filed: Mar. 20, 1992

[51] Int. Cl.$^5$ ..................... G01D 18/00; G01B 15/00
[52] U.S. Cl. ..................................... 367/13; 73/1 DV
[58] Field of Search ......................... 367/13; 73/1 DV

[56] References Cited
U.S. PATENT DOCUMENTS
4,903,523  2/1990  Flynn ................................ 73/1 DV

Primary Examiner—Daniel T. Pihulic
Attorney, Agent, or Firm—Eric R. Katz

[57] ABSTRACT

An ultrasonic calibration block for standardizing an output of a pulse-echo ultrasonic inspection system is provided with an insonification surface for receiving ultrasonic pulses from the inspection system and a plurality of reflective interfaces stacked on top of one another and positioned at different distances from the insonification surface, each reflective interface having a different and characteristic reflectivity. A method of calibrating the output of the inspection system, using the calibration block, employs standard waveforms generated by insonifying the calibration block to generate a look-up table of standard waveform amplitudes related to a standardized output of the inspection system for a given material of a part to be inspected.

10 Claims, 6 Drawing Sheets

CALIBRATION BLOCK AND METHOD FOR AN ULTRASONIC SYSTEM

BACKGROUND OF THE INVENTION

1. Field of the Invention

The present invention generally relates to an ultrasonic reference or calibration block applicable to a broad range of different materials and material thicknesses as well as to a method for calibrating an ultrasonic inspection system. More particularly, the present invention relates to a such a calibration block and method which reliably and accurately calibrates, for standardization, the signal output of an ultrasonic system.

2. Background Discussion

Digital ultrasonic data acquisition systems are widely used in the non-destructive evaluation (NDE) of materials using pulse-echo ultrasonics. Flaws detectable and charactereristical using pulse-echo ultrasonics include, but are not limited to, material voids, porosity, cracks and delaminations.

Figure 1:
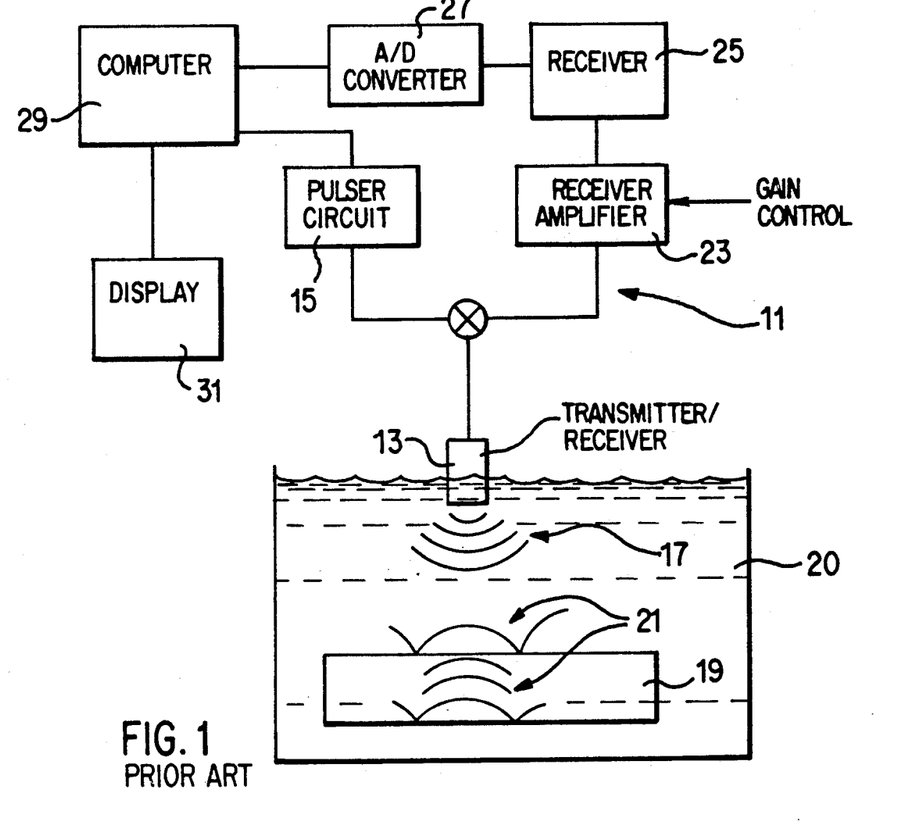
FIG. 1 is a block diagram illustrating an ultrasonic inspection system.

As best seen in FIG. 1, such an inspection system, generally indicated at 11, employs a piezoelectric transducer 13 which functions as a transmitter/receiver is stimulated by electrical signals from a pulser circuit 15 so as to generate pulses 17 of ultrasonic sound energy which are transmitted through a coupling fluid (water) toward a part 19 to be evaluated. To obtain the best results, it is preferred that the angle of incidence of the ultrasonic pulses 17 be normal to the surface of the part 19 and the part 19 be submerged in water 20.

As a result of this insonification of the part, some of the incident ultrasonic energy is reflected from the proximal or front surface of the part and some of the pulse is reflected from the distal or back surface of the part in the form of sonic echo returns. However, not all the ultrasonic energy is directly reflected from the proximal and distal surfaces. In this regard, some energy is trapped in the material itself and reverberates back and forth between the front and back surfaces of the part, portions of this trapped energy being emitted on a non-random basis from either the front or back surface. Further, some of the energy is transmitted entirely through the part.

The piezoelectric transducer 13 also detects the sonic echo signals 21 received back from the insonified part 19. These echo signals 21 are converted into electrical signals by the piezoelectric transducer 13, amplified by a receiver or input amplifier 23 and provided to a receiver 25. The output of the receiver 25 is preferably converted into digital form by an analog-to-digital converter 27 for analysis by a computer 29 to non-destructively evaluate the material of the part. The computer is typically provided with a display 31 for at least viewing the signals generated by the receiver 25 and also for plotting the results of the processing.

Figure 2:
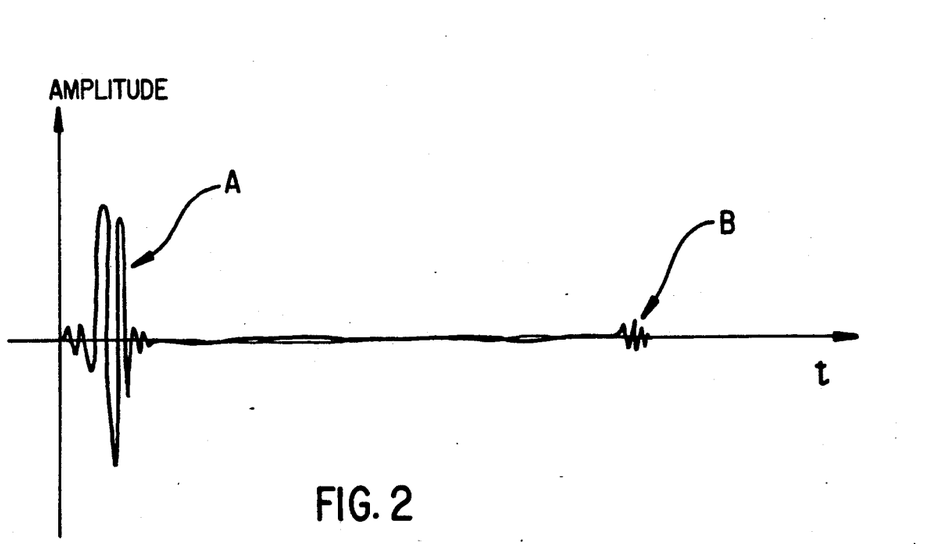
FIG. 2 illustrates a typical waveform generated by insonifying a part being inspected by the system of FIG. 1.

Because the ultrasonic pulses are reflected from interfaces at different depths, i.e., the front and back surface interfaces of the part, the echo signals from each of the interfaces are spaced in time as to their arrival at the piezoelectric transducer 13. Therefore, each of these different echo returns can be distinguished from one another and viewed as well as plotted on the display 31, the type of material insonified determining the configuration of the echo returns. FIG. 2 illustrates the returns from a piece of acrylic, waveform A representing the reflection from the proximal or front surface of the part and waveform B representing the reflection from the distal or back surface. Typically, it is waveform B which is used to analyze the material of the part 19 because the reflection responsible for waveform B has passed entirely through the part and thus, has encountered all deflects.

The receiver output signals must have some minimum threshold amplitude in order for the computer 29 to be able to use the receiver output signals to detect material flaws in the part 19 because the receiver 25 is usable over only a defined dynamic range and the analog-to-digital 27 converter has a fixed resolution, typically 8 to 10 bits. Therefore, gain G is used as an offset to bring a desired signal within the usable dynamic range of the analog-to-digital converter 21 of the receiver 25. As a result, the gain G of the receiver input amplifier 23 must be set or calibrated in order to provide the required output level of the receiver 25.

To conduct a non-destructive evaluation of a part using an ultrasonic inspection system, the output of the ultrasonic system is first calibrated. The calibration is achieved by insonifying a flawless piece of the material from which the part is made, i.e., a standard.

In calibrating the system, the amplitude of the output signal of the receiver 25 is adjusted by varying the gain G of the receiver amplifier 23 until the displayed signal, i.e., the receiver signal, reaches some arbitrary value, for example, 90% of full scale. 90% full scale is typically chosen as the arbitrary value to provide the desired degree of sensitivity in order to obtain useful results during analysis by the computer.

The adjusted output of the input amplifier 23 is then fixed by setting its gain G at the level that results in the 90% of full scale reading on the display and this output amplitude is used as the standard amplitude level for evaluating all other portions of the part. The frequency and amplitude of the ultrasonic energy received back from each portion of the part is then analyzed, in comparison with the frequency and amplitude response of the sonic energy received from the flawless standard made of the material of the part, to determine the presence or absence of flaws. In this regard, an overall lowering in amplitude of the output of the inspection system, i.e., output of the receiver 25, typically indicates the presence of some kind of material defect.

Because certain material flaws are visible only within specific frequency ranges, it is often necessary to vary the frequency of output pulse of the ultrasonic transducer to obtain the best results. Therefore, it is necessary to have accurate information on the frequency spectrum of the output pulse of the transducer.

Further, different materials have different ultrasonic properties, and, as a result, have different brightnesses, i.e., varying degrees of transmission, attenuation and reflectivity, when insonified with an ultrasonic pulse. Therefore, in order to obtain useful results, it is often necessary to vary the output amplitude of the receiver signal by varying the gain of the receiver amplifier in dependence on the type material and thickness of the material.

Because the output of the inspection system can change from day to day due to drift, component aging, or the like, a given gain setting of the receiver amplifier on one day may not result in the same output amplitude level of the receiver signals on another day. As a result, the output of the inspection system must be standardized on at least a daily basis, sometimes hourly. Additionally, the amplitude level for a given gain setting of the receiver amplifier can vary from inspection system to inspection system which results in the need to be able to accurately and reliably calibrate the output level of any ultrasonic inspection system to a precise standard for comparison of results from different ultrasonic inspection systems.

When the material of the part being evaluated has well-known ultrasonic properties, for example, metal or plastic materials, which are isotropic, have uniform ultrasonic properties which do not change for a given orientation of the lattice structure relative to the ultrasonic transducer, it is fairly easy to calibrate the output amplitude of the system using any piece of the well-known material as a standard. As a result, different tests run on different inspection systems can be compared with one another with a high degree of reliability when the output level of each inspection system is calibrated to the same standard using different pieces of the same material. However, problems are often encountered when the ultrasonic properties of the material of the part are unknown. This problem is typically encountered when using NDE techniques to analyze new and different composite materials which have a wide variation in ultrasonic properties and are not abundantly available. In order to properly calibrate the ultrasonic inspection system when analyzing a part made of a material having unknown ultrasonic properties, a portion of the part under inspection, which is believed to be flawless, i.e., the best area, is insonified and used as the standard for calibration of the ultrasonic inspection system. Thereafter, the portion of the part believed to be flawless is archived as the standard for further reference. This approach is somewhat cumbersome in practice, requiring the storage and indexing of a large number of material samples which may or may not be readily available in quantity.

Figure 3:
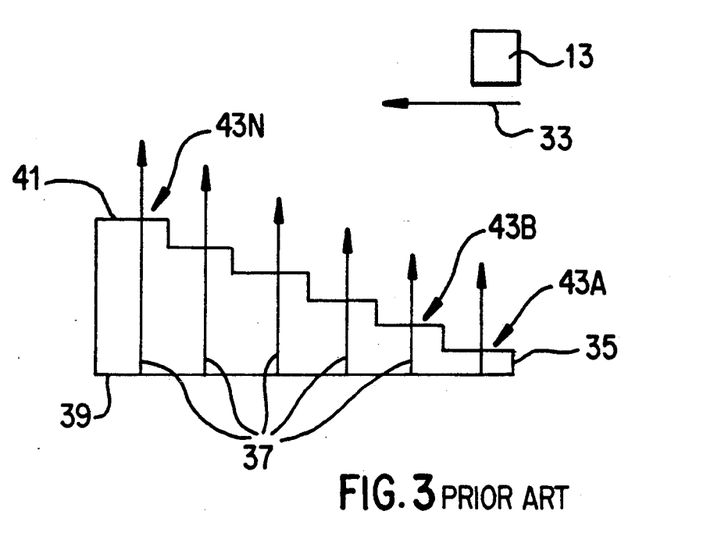
FIG. 3 is a side view illustrating the operation of a known calibration block.

Alternatively, a calibration block is used as the standard of calibrating the output of the inspection system. An example of a known calibration block arrangement is schematically indicated in FIG. 3. The arrangement comprises an ultrasonic piezoelectric transducer 13 which is scanned in the direction of arrow 33 across a step wedge calibration block 35. Because of the step wedge configuration of the block 33, the ultrasonic echo returns 37 received back from the distal surface 39 of the block 33 travel through increasing quantum amounts of material resulting echo returns of decreasing brightness.

However, drawbacks are encountered by such a scanning arrangement which requires that the position of the piezo-electric transducer 13 be maintained at a constant distance from the distal surface 39 of the block 33 during the entire scanning process in order to obtain useful result. Further, the scanning process introduces unwanted errors and complexities during the calibration process as opposed to a calibration method which requires the insonification of a calibration block at but a single point. Moreover, any variation in the distance between the transducer 13 and the distal surface 39 during scanning results in non-standard echo returns from the distal surface 39. As a consequence, this approach results in a calibration having a limited dynamic range and ultrasonic beam characteristics which may not compare to the actual part being inspected.

Therefore, the need has arisen for an ultrasonic reference or calibration block standard which can be used to calibrate the output of an ultrasonic inspection system to a given standard output, which standard can then be used with materials having unknown ultrasonic properties.

SUMMARY OF THE INVENTION

Accordingly, it is an object of the present invention to provide both a method and ultrasonic reference or calibration block for calibrating the output of an ultrasonic inspection system for NDE testing to a precise standard regardless of the type of material being analyzed by the inspection system.

It is another object of the present invention to provide a method and calibration block wherein the output an ultrasonic inspection system can be reliably and accurately calibrated for standardization of the inspection system.

These and other objects, advantages and features are achieved, according to preferred embodiments of the present invention, by an ultrasonic reference or calibration block applicable to a broad range of different materials and material thicknesses. The calibration block comprises a plurality of reflective interfaces stacked on top of one another and positioned at different distances from a proximal surface of the block, each reflective interface having a different reflectivity. In this regard, the calibration block is preferably constructed so that each reflective interface produces, for example, a different and decreasing reflectivity or reflection amplitude as viewed by the inspection system. Because the reflective interfaces of the calibration block of the present invention are stacked on top of one another, a plurality of standard echo return waveforms are generated upon insonification of the block using a stationary piezoelectric transducer which functions as a transmitter/receiver, each standard waveform being representative of an echo return from a different one of the plurality of reflective interfaces.

Because each interface has a different reflectivity, each standard waveform has a different amplitude of echo reflection at the given output of the inspection system. Further, due to the fact that each of the interfaces is positioned at a different distance from the inspection system, the plurality of standard waveforms are received at different time intervals by the piezoelectric transducer and are non-overlapping.

One particularly advantageous feature of the calibration block of the present invention is the elimination of the need to scan the piezoelectric transmitter/receiver across the face of the block in order to obtain reflections of varying intensity. This feature provides for a high reliability in generating reproducible standard results from the calibration block.

Other objects, advantages and features are achieved, according to preferred embodiments of the present invention, by a method of standardizing the output of an ultrasonic inspection system. The method comprises the steps of: insonifying a first part, deemed to be materially acceptable (essentially flawless), and sensing an echo return from the part. Thereafter, a waveform, representative of the echo return reflected from a reflective interface of the part at a given output of the ultrasonic inspection system, is generated and the output of the inspection system is adjusted until an amplitude of the part echo waveform is sufficiently large to permit analysis thereof.

Subsequently, a calibration block, having a plurality of reflective interfaces, stacked one on top of another and positioned at different distances from the inspection system, is insonified at the adjusted output of the inspection system.

The echo returns from the plurality of reflective interfaces of the calibration block are sensed and a plurality of standard waveforms are generated, each standard waveform being representative of an echo return from a different one of the plurality of reflective interfaces. Because each interface has a different reflectivity, each standard waveform has a different amplitude of echo reflection at the adjusted output of the inspection system.

The operator views the plurality of standard waveforms on the display of the inspection system and selects the one of the plurality of standard waveforms having a maximum amplitude nearest to the amplitude of the part echo waveform without being saturated. The value of the maximum amplitude of the selected one of the plurality of standard waveforms is noted, i.e , stored in a look-up table or the like. Then, during subsequent inspections of a part similar to the first part, the calibration block is first insonified and the output of the inspection system is adjusted until the maximum amplitude of the previously selection one of the plurality of standard waveforms matches the previously noted maximum amplitude. As a result, the output of the inspection system is calibrated to a standard output for all parts similar to the first part.

DESCRIPTION OF THE PREFERRED EMBODIMENTS

The novel features which are believed to be characteristic of the invention, both as to its organization and method of operation, together with further objects and advantages thereof, will be better understood from the following description in connection with the accompanying drawings in which the presently preferred embodiments of the invention are illustrated by way of examples. It is to be expressly understood, however, that the drawings are for purposes of illustration and description only and are not intended as a definition of the limits of the invention.

Calibration Block

Figure 4:
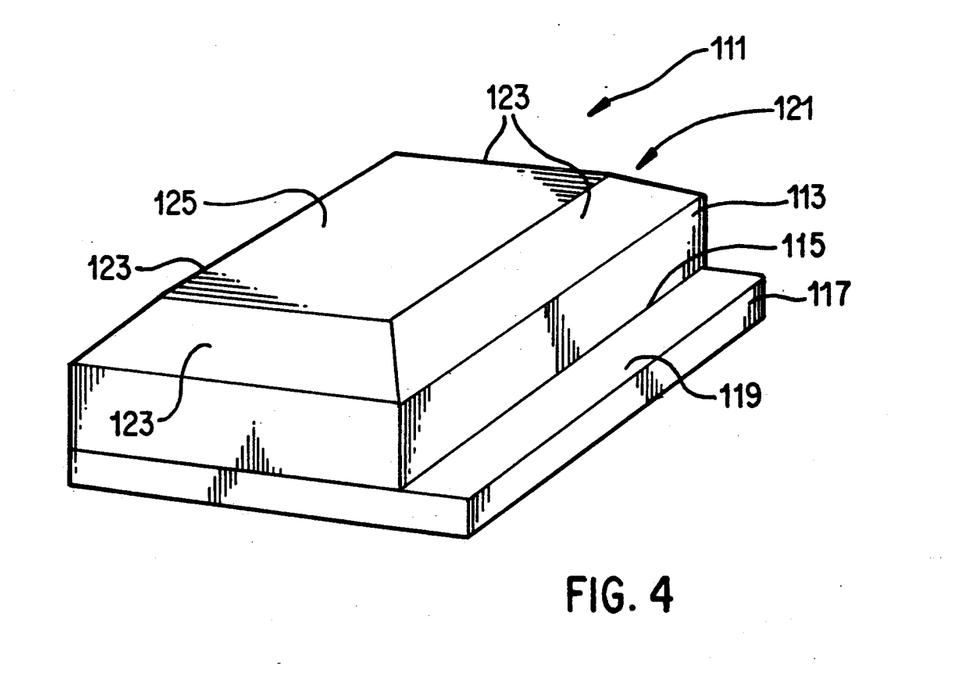
FIG. 4 is a perspective view of a calibration block according to one embodiment of the present invention.

Referring to FIG. 4, one embodiment of the calibration block of the present invention, generally indicated at 111, is illustrated. The calibration block 111 comprises an upper block 113 made of a plastic material, for example, acrylic bonded over its entire lower surface by an adhesive 115 to a lower plate 117 of, for example, aluminum. The plate 117 is, for example, somewhat larger than the block 113 on one side thereof in order to provide a mounting lip 119 for mounting the calibration block 111.

The upper surface 121 of the upper block 113 has chamfered or beveled edges 123 which surround a flat central region 125. Preferably, the edges 123 are chamfered at an angle of at least 2 degrees to about 5 degrees relative to the flat central region 2 degrees being preferred. As will be explained more fully hereinafter, the chamfered edges 123 are employed to check normality, i.e., adjust the angle of incidence of the ultrasonic pulses at the upper surface 121, to assure that the beam of ultrasonic pulses strikes the upper surface 121 at a right angle.

The ultrasonic properties of the materials chosen to comprise the calibration block 111 are such that the difference in "brightness" when insonified by ultrasonic pulses, between the upper block 113 and the lower plate 117 is substantially equal to the different in reflectivity between the upper block 113 and the water in which a sample part to be inspected is normally immersed. In this regard, it should be noted that the term "brightness" as used herein 11 is synonymous to the term "impedance mismatch". Because the calibration block 111 is typically immersed in water during use, the lower plate 117, for example, is protected against corrosion by anodizing.

Further, the adhesive 115 which bonds the upper block 113 to the lower plate 117 is chosen to be as thin as possible and to closely matched the ultrasonic properties of the plastic material which comprises the upper block 113. Additionally, the relative thicknesses of the block 113 and the plate 117 are chosen so that the echo returns from each reflective interface of the calibration block 111 are suitably separated in time so as to be easily distinguishable.

Figure 5:
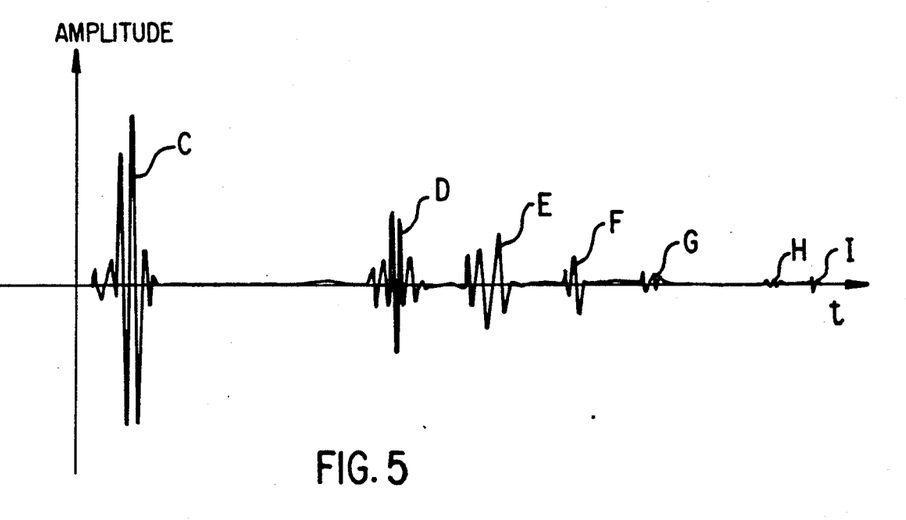
FIG. 5 illustrates a typical waveform generated by insonifying the calibration block of FIG. 4.

As a result of these above-noted relationships between the materials used to form the upper block 113 and the lower plate 117, their relative thicknesses and method of bonding, the echo signals received back from the calibration block 111 are spread over a broad dynamic range so that at least one echo signal will be applicable to almost any type of echo return as best seen in FIG. 5.

Referring to FIG. 5, a plurality of standard echo return waveforms C-I are illustrated which are generated upon insonification of the flat central region 125 of the calibration block 111 using a stationary piezoelectric transmitter/receiver. Each standard waveform C-I is representative of an echo return from one of the plurality of reflective interfaces.

Figure 6:
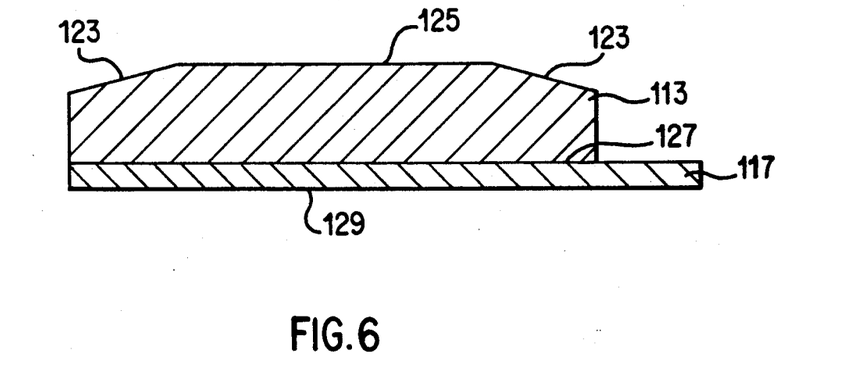
FIG. 6 is a side view, in section, of the calibration block of FIG. 4.

Referring to FIG. 6, a cross-sectional view of the calibration block 111 is provided which illustrates the various reflective interfaces and their relation to the waveforms of FIG. 5. In this regard, waveform C is generated by reflections from the flat region 125, waveform D is generated at the interface 127 between block 113 and plate 117 and waveform E is generated by the back surface 129 of the plate 117.

The remaining waveforms F-I are generated by internal reflections between interfaces which eventually are radiated out of the calibration block 111 and back to the inspection system. For example, these waveforms are generated by reflections (one, two, three . . . and more times) between the flat surface 125 and the interface 127 or between the flat surface 126 and the back surface 129 or between the interface 127 and the back surface 129 and so forth which are eventually transmitted back out of the upper surface 121 and back to the inspection system.

Because each interface of the calibration block 111 has a different reflectivity, and different echo return paths involve travelling through different thicknesses of material, each standard waveform has a different amplitude of echo reflection at the given output of the inspection system. In light of the degree of sensitivity of inspection systems currently available, it is preferred that the small amplitude of a standard waveform (waveform I) be at least 0.5% of the amplitude of the largest amplitude of a standard waveform (waveform A), and more preferable at least 0.10%. Further, each of the interfaces is positioned at a different distance from the inspection system so that the plurality of standard waveforms are received at different time intervals by the piezoelectric transmitter/receiver and are non-overlapping.

EXAMPLE

A 0.250 inch thick, 2.5 inch wide and 4 inch long block of optical grade, craze resistant acrylic having a finish A is provided with beveled edges (chamfered edges 123) which are one (1) inch wide so as to form a flat upper surface of 1.5 by 3 inches. Also provided is a 0.125 inch thick, 3 inch wide and 4 inch long plate of bare 2024 aluminum (no cladding). The aluminum plate is, for example, anodized for corrosion protection. The aluminum plate is then bonded to the acrylic block using an acrylic adhesive such as methyl methacrylate adhesive.

Operation

Figure 7A:
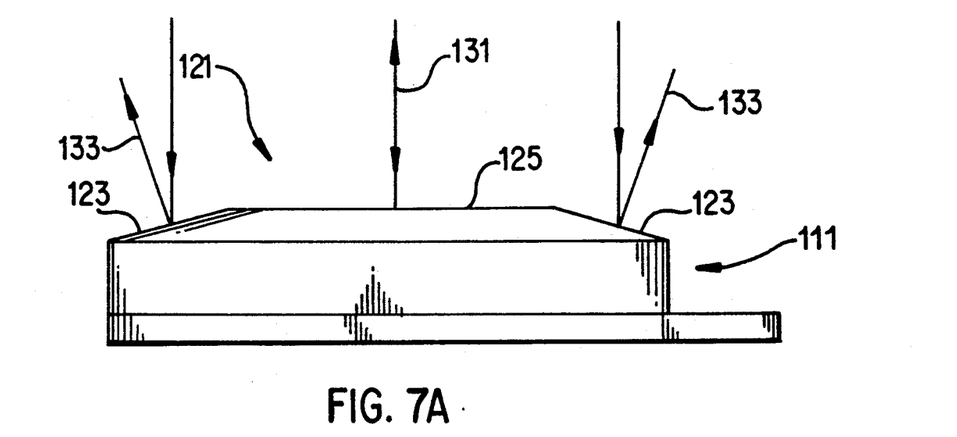
FIGS. 7A-7C illustrate one embodiment of the normalization method of the present invention.
Figure 7B:
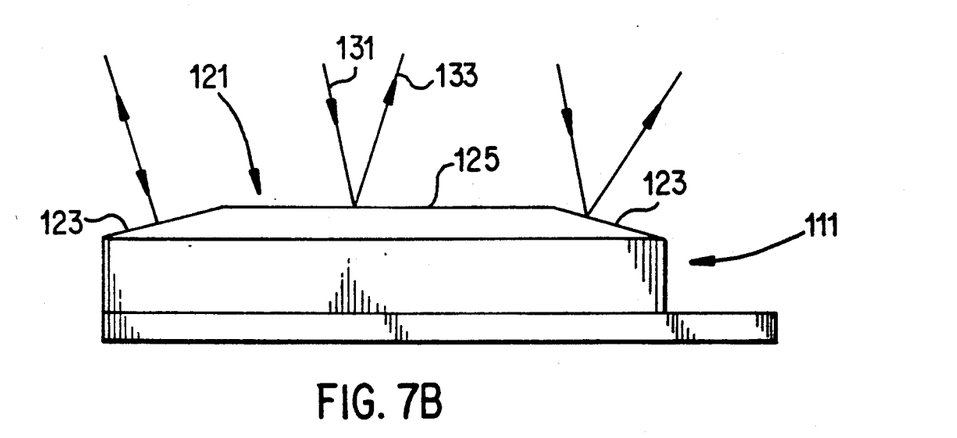
Figure 7C:
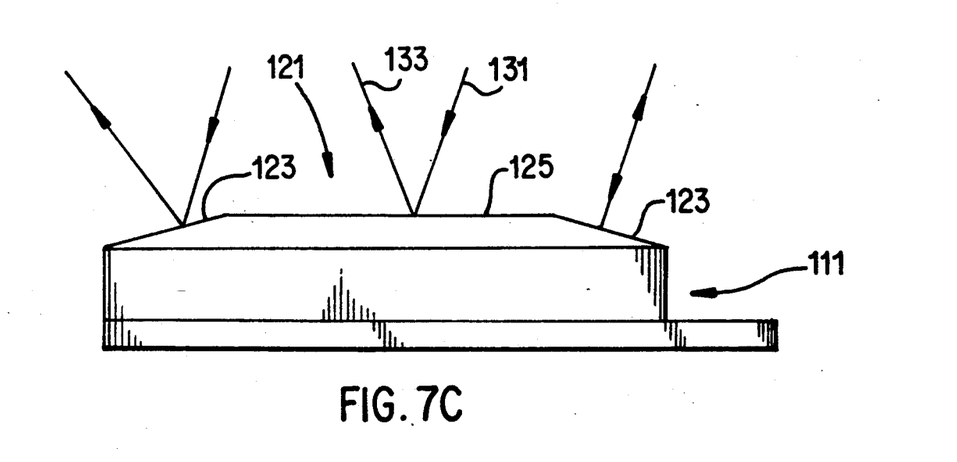
Figure 8:
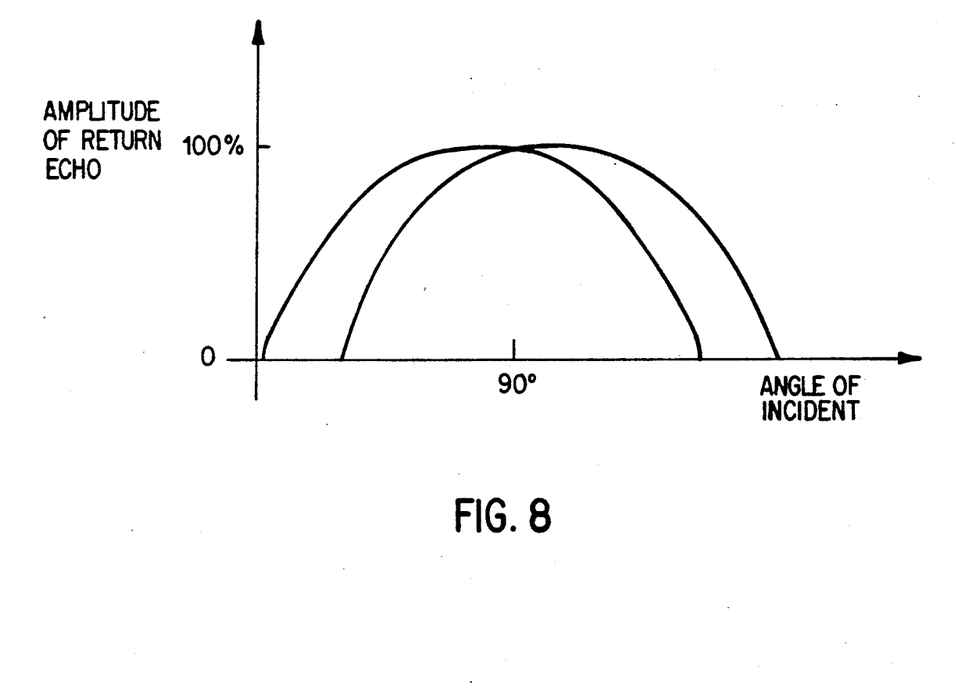
FIG. 8 is a graph of amplitude verses angle of incidence which illustrates the rounding off of the normality peak at near normal incidence.

The normality or perpendicularity of the incident ultrasonic pulse to surface to be interrogated is a critical aspect of pulse-echo ultrasonics in order to generate the strongest echo returns possible for detection as well as for standardization or repeatability of results. Typically, normality is found by an angled sweep "peak-up" in two planes looking for the maximum amplitude of the return echo in each of the planes. With focused beams, this approach can introduce significant errors because the normality peak is substantially rounded at a 90 degree angle of incidence by the angular spectrum of the transducer as best seen in FIG. 7. Therefore, it is hard to distinguish where the peak of the curve is really located.

One particular advantageous feature of the calibration block 111 is the provision of beveled edges 123 which are employed to assess the balance of the normality of the incident beam of ultrasonic pulses in two planes. Referring to FIG. 7A, when the incident beam 131 is normal to the flat region 125 of the upper surface 121, the signal returns 133 are reduced and equal. However, when the incident beam 131 is slightly off normal, as seen in FIGS. 7B–7C, the signal from one of the beveled edges 123 will be larger than the other and unbalanced. By adjusting the angular orientation of the piezoelectric transducer transmitter/receiver until the return signals from the edges 123 are balanced, normality of the incident beam of ultrasonic pulses as assured and angular errors are reduced as well as variability.

Once the normality of the transducer is set, the standard waveforms of FIG. 5 are generated by insonifying the flat region 125 of the upper surface 121 of the calibration block 111. These standard waveforms are used to calibrate the output of the inspection system as will be more fully described in the following.

Figure 9:
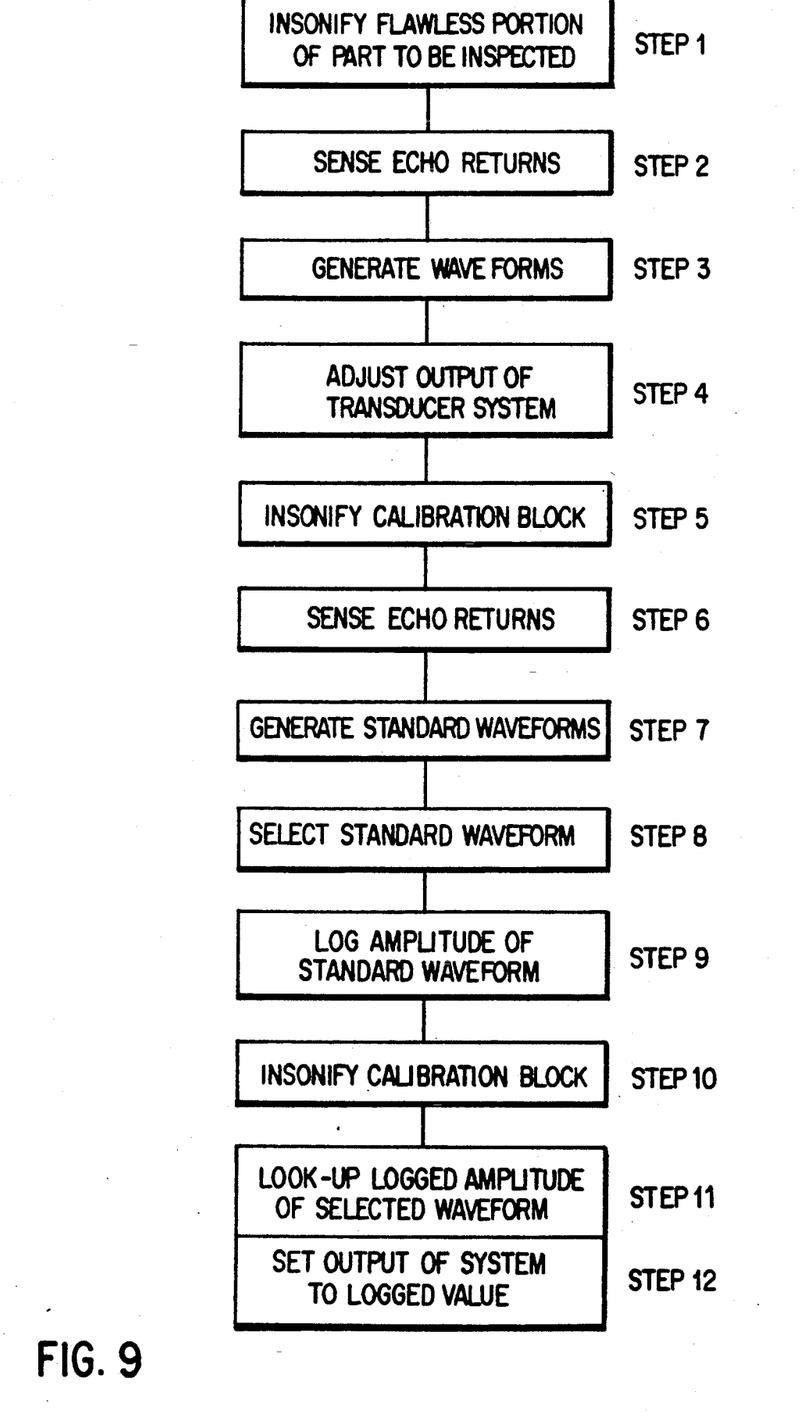
FIG. 9 illustrates one embodiment of the method of standardizing the output of an ultrasonic inspection system.

Referring to FIG. 9, one embodiment of the method of standardizing the output of an ultrasonic inspection system of the present invention is illustrated. In step 1 of the method a flawless portion of a first part, which has already been inspected and deemed acceptable, is insonified and in step 2 the echo return from the first part is sensed. Thereafter, a part echo waveform, representative of the echo return reflected from a reflective interface of the part at a given output of the ultrasonic inspection system, is generated in step 3 and, in step 4, the output of the inspection system is adjusted until an amplitude of the part echo waveform is sufficiently large to permit analysis thereof.

In step 5, the calibration block of the present invention, having a plurality of reflective interfaces stacked one on top of another and positioned at different distances from the inspection system, is insonified at the adjusted output of the inspection system as described previously.

The echo returns from the plurality of reflective interfaces of the calibration block are sensed in step 6 and a plurality of standard waveforms are generated in step 7, each standard waveform being representative of an echo return from a different one of the plurality of reflective interfaces. As noted above, because each interface has a different reflectivity and echo return paths from each of the interfaces pass through different amounts of material, each standard waveform has a different amplitude of echo reflection at the adjusted output and characteristic of the inspection system.

The operator views the plurality of standard waveforms on the display of the inspection system and in step 8, selects the one of the plurality of standard waveforms having a maximum amplitude nearest to the amplitude of the part echo waveform without being saturated. The value of the maximum amplitude of the selected one of the plurality of standard waveforms is noted and stored, for example, logged in a look-up table in step 9.

During subsequent inspections of similar parts, the calibration block is first insonified in step 10 and in step 11 the previously stored and logged value for the part is looked up. Then in step 12, the output of the inspection system is adjusted until the maximum amplitude of the previously selection one of the plurality of standard waveforms matches the previously noted maximum amplitude.

While the invention has been described with reference to particular embodiments, it should be understood that the embodiments are merely illustrative as there are numerous variations and modifications which may be made by those skilled in the art. Thus, the invention is to be construed as being limited only by the spirit and scope of the appended claims.

We claim:

1. A method of standardizing an output of an ultrasonic inspection system, the method comprising the steps of:
   insonifying a first part using an ultrasonic transducer of the inspection system, the first part being deemed acceptable;
   sensing an echo return from the part;
   generating a part echo waveform representative of the echo return reflected from the part at a given output of the ultrasonic inspection system;

adjusting the output of the inspection system until an amplitude of the part echo waveform is sufficiently large to permit analysis thereof;

insonifying, at the adjusted output of the inspection system, a calibration block having a plurality of reflective interfaces at different distances from the inspection system, each reflective interface having a different and decreasing reflectivity;

sensing echo returns from the plurality of reflective interfaces of the calibration block;

generating a plurality of standard waveforms each representative of an echo return from the calibration block, each standard waveform having a different amplitude and characteristic of echo reflection at the adjusted output of the inspection system, the plurality of standard waveforms being essentially non-overlapping and each having a given maximum amplitude;

selecting one of the plurality of standard waveforms having a maximum amplitude nearest to the amplitude of the part echo waveform;

storing the maximum amplitude of the selected one of the plurality of standard waveforms with an identity of the part; and during subsequent inspections of a part similar to the first part, insonifying the calibration block and adjusting the output of the inspection system until the maximum amplitude of the selection one of the plurality of standard waveforms matches the noted maximum amplitude.

2. A method according to claim 1, wherein the ultrasonic transducer is stationary during the step of insonifying the calibration block.

3. A method according to claim 1, wherein the step of storing further includes storing, in a look-up table, the maximum amplitude of the selected standard waveform indexed to a material of the part.

4. An ultrasonic calibration block for standardizing an output of an ultrasonic inspection system, the block comprising:

an insonification surface for insonification with ultrasonic pulses from the inspection system;

a plurality of reflective interfaces stacked on top of one another and positioned at different distances from the insonification surface, each reflective interface having a different reflectivity.

5. A block according to claim 4, wherein each reflective interface has decreasing reflectivity as viewed from the insonification surface of the block.

6. A block according to claim 5, wherein a plurality of standard echo return waveforms are generated upon insonification of the block, wherein each standard waveform has a different amplitude of echo reflection at a set output of the inspection system and wherein the plurality of standard waveforms are received at different time intervals by the inspection system and are non-overlapping.

7. A block according to claim 4, wherein the insonification surface has at least one beveled edge.

8. A block according to claim 4, wherein the plurality of reflective interfaces are formed by a block of material affixed to a plate of material by a layer of adhesive, wherein the block of material has a different impedance that an impedance of the plate of material and the adhesive has an impedance similar to the impedance of the block of material.

9. A block according to claim 8, wherein a thickness of the block and plate are chosen so that reflections from the plurality reflective interfaces are spaced in time.

10. A block according to claim 8, wherein the material of the block is a plastic and the material of the plate is a metal.

* * * * *